(12) United States Patent
Brizius

(10) Patent No.: US 9,181,287 B2
(45) Date of Patent: Nov. 10, 2015

(54) REGIOREGULAR COPOLYMERS AND METHODS FOR MAKING SAME

(71) Applicant: EMPIRE TECHNOLOGY DEVELOPMENT LLC, Wilmington (DE)

(72) Inventor: Glen Leon Brizius, Augusta, GA (US)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 14/567,875

(22) Filed: Dec. 11, 2014

(65) Prior Publication Data
US 2015/0094484 A1 Apr. 2, 2015

Related U.S. Application Data

(63) Continuation of application No. 13/811,758, filed as application No. PCT/US2012/054147 on Sep. 7, 2012, now Pat. No. 8,937,148.

(51) Int. Cl.
| | | |
|---|---|---|
| C08G 75/06 | (2006.01) |
| C07F 9/28 | (2006.01) |
| C08G 61/02 | (2006.01) |
| C07F 7/08 | (2006.01) |
| C08F 138/00 | (2006.01) |
| C07F 9/40 | (2006.01) |
| C07F 5/00 | (2006.01) |

(52) U.S. Cl.
CPC ... *C07F 9/28* (2013.01); *C07F 5/00* (2013.01); *C07F 7/0818* (2013.01); *C07F 7/0827* (2013.01); *C07F 9/4056* (2013.01); *C08F 138/00* (2013.01); *C08G 61/02* (2013.01); *C08G 2261/1424* (2013.01); *C08G 2261/212* (2013.01); *C08G 2261/3328* (2013.01); *C08G 2261/3422* (2013.01); *C08G 2261/415* (2013.01)

(58) Field of Classification Search
None
See application file for complete search history.

(56) References Cited

U.S. PATENT DOCUMENTS

| | | | |
|---|---|---|---|
| 4,360,686 | A | 11/1982 | Wang et al. |
| 4,537,974 | A | 8/1985 | Lau |
| 4,587,315 | A | 5/1986 | Lau |
| 5,290,939 | A | 3/1994 | Sedelmeier et al. |
| 5,653,914 | A | 8/1997 | Holmes et al. |
| 7,084,231 | B2 | 8/2006 | Cho et al. |
| 7,868,126 | B2 | 1/2011 | Kageyama et al. |
| 7,888,453 | B2 | 2/2011 | Choi et al. |

(Continued)

FOREIGN PATENT DOCUMENTS

| | | |
|---|---|---|
| AT | 147059 T | 1/1997 |
| AT | 487752 T | 11/2010 |

(Continued)

OTHER PUBLICATIONS

Jian et al. "Preparative Fluorous Mixture Synthesis of Diazonium-Functionalized Oligo(phenylene vinylene)s" J. Org. Chem. 2005, 70, 3396-3424.*

(Continued)

*Primary Examiner* — Robert S Loewe
(74) *Attorney, Agent, or Firm* — Pepper Hamilton LLP

(57) ABSTRACT

Methods for producing regioregular poly(aryl ethynyl)-poly (aryl vinyl) and monomers for preparing the regioregular poly(aryl ethynyl)-poly(aryl vinyl) polymers are described herein. Regioregular poly(aryl ethynyl)-poly(aryl vinyl) are useful for electronics, among other things.

12 Claims, 1 Drawing Sheet

(56) References Cited

U.S. PATENT DOCUMENTS

| | | | |
|---|---|---|---|
| 7,947,340 | B2 | 5/2011 | Ikehira et al. |
| 2002/0193532 | A1 | 12/2002 | Ikehira et al. |
| 2005/0176915 | A1 | 8/2005 | Cho et al. |
| 2007/0197768 | A1 | 8/2007 | Choi et al. |
| 2008/0249280 | A1 | 10/2008 | Kageyama et al. |
| 2009/0042841 | A1 | 2/2009 | Leonardi et al. |
| 2010/0283006 | A1 | 11/2010 | Ajayaghosh et al. |
| 2011/0187969 | A1 | 8/2011 | Ikehira et al. |

FOREIGN PATENT DOCUMENTS

| | | | |
|---|---|---|---|
| AT | 539075 | T | 1/2012 |
| AU | 5706994 | A | 7/1994 |
| AU | 661722 | B2 | 8/1995 |
| AU | 691344 | B2 | 5/1998 |
| AU | 691345 | B2 | 5/1998 |
| AU | 2008282032 | A1 | 2/2009 |
| CA | 2080683 | A1 | 4/1993 |
| CA | 2694359 | A1 | 2/2009 |
| CN | 101208371 | A | 6/2008 |
| CN | 101821256 | A | 9/2010 |
| CN | 101208371 | B | 8/2011 |
| DK | 0542671 | T3 | 1/1997 |
| DK | 2178858 | T3 | 3/2012 |
| EP | 0542671 | B1 | 1/1997 |
| EP | 1842868 | B1 | 11/2010 |
| EP | 2258805 | A3 | 10/2011 |
| EP | 2258806 | A3 | 10/2011 |
| EP | 2258807 | A3 | 10/2011 |
| EP | 2258808 | A3 | 10/2011 |
| EP | 2258809 | A3 | 10/2011 |
| EP | 2178858 | B1 | 12/2011 |
| EP | 1245659 | B1 | 3/2012 |
| ES | 2380165 | T3 | 5/2012 |
| FI | 924651 | A | 4/1993 |
| GR | 3022221 | T3 | 4/1997 |
| HK | 1141788 | A1 | 9/2012 |
| HR | P20120225 | T1 | 4/2012 |
| HU | T66250 | A | 4/1993 |
| JP | 5213808 | A | 8/1993 |
| JP | 2003171659 | A | 6/2003 |
| JP | 2007182458 | A | 7/2007 |
| JP | 2007277558 | A | 10/2007 |
| JP | 2008019443 | A | 1/2008 |
| JP | 2010535165 | A | 11/2010 |
| JP | 2011241226 | A | 12/2011 |
| JP | 2012012608 | A | 1/2012 |
| KR | 20020076182 | A | 10/2002 |
| KR | 20040091851 | A | 11/2004 |
| KR | 20070084855 | A | 8/2007 |
| KR | 20080015449 | A | 2/2008 |
| KR | 20100052507 | A | 5/2010 |
| KR | 101018219 | B1 | 2/2011 |
| MX | 9205989 | A | 8/1993 |
| MY | 144577 | A | 10/2011 |
| NO | 180441 | B | 1/1997 |
| NZ | 224751 | A | 2/1995 |
| NZ | 582934 | A | 10/2011 |
| PL | 2178858 | T3 | 7/2012 |
| PT | 2178858 | E | 2/2012 |
| RS | 52167 | B | 8/2012 |
| RU | 2095339 | C1 | 11/1997 |
| SG | 92833 | A1 | 11/2002 |
| SI | 2178858 | T1 | 3/2012 |
| TW | 1306891 | B | 3/2009 |
| WO | WO 94/15441 | A1 | 7/1994 |
| WO | WO2006/137145 | A1 | 12/2006 |
| WO | WO2009/015897 | A1 | 2/2009 |
| WO | WO2009/084006 | A1 | 7/2009 |
| ZA | 9208003 | A | 4/1993 |

OTHER PUBLICATIONS

International Search Report and Written Opinion for PCT/US2012/054147 dated Nov. 20, 2012.

Al-Ibrahim et al., Phenylene-ethynylene/phenylene-vinylene hybrid polymers: optical and electrochemical characterization, comparison with poly[2-methoxy-5-(3',7'—dimethyloctyloxy)-1,4-phenylene vinylene] and application in flexible polymer solar cells, *Thin Solid Films* (Nov. 23, 2004), 474:201-210.

Arbusov, Zhurnal Russkogo fiziko Khimicheskogo Obshchestva, *J. Russ. Phys. Chem. Soc.* (1906), 38:687 (English translation unavailable).

Bag et al., Click Reagent Version of Sonogashira Coupling Protocol to Conjugated Fluorescent Alkynes with No or Reduced Homocoupling, *J. Org. Chem.* (Mar. 8, 2011), 76(7):2332-2337 (Abstract).

Breitenkamp et al., Aggregation of Poly(*p*-phenylene ethynylene)s Containing Nonplar and Amine Side Chains, *Macromolecules* (Jan. 16, 2004), 37(3):1163-1165 (Abstract).

Brizius et al., Alkyne Metathesis with Simple Catalyst Systems: Efficient Synthesis of Conjugated Polymers Containing Vinyl Groups in Main or Side Chain, *J. Am. Chem. Soc.* (Dec. 2, 2000), 122:12435-12440.

Bunz, Poly(aryleneethynylene)s: Syntheses, Properties, Structures, and Applications, *Chem. Rev.* (Mar. 14, 2000), 100(4):1605-1644 (Abstract).

Chen et al., Polyalkylthiophenes with the smallest bandgap and the highest intrinsic conductivity, *Synthetic Metals* (Sep. 15, 1993), 60(2):175-177 (Abstract).

Curtis et al., Reversible *n*-Doping of Poly(nonylbithiazole) and Oligomeric Model Compounds. Application as a Li Battery Electrode, *Macromolecules* (Jan. 13, 1998), 31(1):205-207 (Abstract).

DAS, Printed electronics, is it a niche?, http://www.electronicsweekly.com/Articles/25/09/2008/44587/printed-electronics-is-it-a-niche.htm, Sep. 25, 2008.

Diez-Barra et al., Synthesis of Novel Cross-Conjugated Dendritic Fluorophores Containing Both Phenylenevinylene and Phenyleneethynylene, *J. Org. Chem.* (Dec. 14, 2002); 68:832-838.

Egbe et al., Anthracene Based Conjugated Polymers: Correlation between Π-Π-Stacking Ability, Photophysical Properties, Charge Carrier Mobility, and Photovoltaic Performance, *Macromolecules* (Jan. 4, 2010), 43(3):1261-1269 (Abstract).

Egbe et al., Arylene-ethynylene/arylene-vinylene copolymers: Synthesis and structure-property relationships, *Progress in Polymer Science* (Oct. 2009), 34(10):1023-1067 (Abstract).

Egbe et al., Alkoxy-substituted poly(arylene-ethynylene)-*alt*-poly(arylene-vinylene)s: synthesis, electroluminescence and photovoltaic applications, *J. Mater. Chem.* (Dec. 14, 2010), 5(21):1338-1349 (Abstract).

Egbe et al., Investigation of the Photophysical and Electrochemical Properties of Alkoxy-Substituted Arylene—Ethynylene/Arylene—Vinylene Hybrid Polymers, *Macromolecules* (Jun. 28, 2003), 36:5459-5469.

Egbe et al., Supramolecular Ordering, Thermal Behavior, and Photophysical, Electrochemical, and Elecroluminescent Properties of Alkoxy-Substituted Yne-Containing Poly(phenylene-vinylene)s, *Macromolecules* (Sep. 8, 2004), 37:7451-7463.

Fazio et al., Bending and shaping: cubics, calamities and columnars, *J. Mater. Chem.* (Oct. 2, 2001), 11:2852-2863 (Abstract).

Gonzalez-Ronda et al., Structural Characterization of Electrooptically Active Poly(nonylbithiazole), *Macromolecules* (Jun. 17, 1999), 32(14):4558-4565 (Abstract).

Grimsdale et al., Synthesis of Light-Emitting Conjugated Polymers for Applications in Electroluminescent Devices, *Chem. Rev.* (Feb. 19, 2009), 109(3):897-1091 (Abstract).

Hide et al., New Developments in the Photonic Applications of Conjugated Polymers, *Acc. Chem. Res.* (Oct. 14, 1997), 30(10):430-436 (Abstract).

Höger, Synthesis of Bromo-iodo-hydroquinone Monoalkyl Ethers, *Liebigs Annalen* (Jan. 27, 2006), 1997(1):273-277 (Abstract).

Kim et al., Control of conformational and interpolymer effects in conjugated polymers, *Letters to Nature* (Jun. 28, 2001), 411:1030-1034 (Abstract).

Kraft et al., Electroluminescent Conjugated Polymers—Seeing Polymers in a New Light, *Angew. Chem. Int. Ed.* (1998), 37:402-428.

(56) References Cited

OTHER PUBLICATIONS

Li et al., The Process of Functional Conjugated Organic Polymers Derived from Triple-Bond Building Blocks, *Macromolecular Chemistry and Physics* (Jun. 17, 2008), 209(15):1541-1552 (Abstract).

McCullough et al., Enhanced electrical conductivity in regioselectively synthesized poly(3-alkylthiophenes), *J. Chem. Soc., Chem. Commun.* (1992), 1:70-72 (Abstract).

McQuade et al., Conjugated Polymer-Based Chemical Sensors, *Chem. Rev.* (Jun. 9, 2000), 100(7):2537-2574 (Abstract).

Nambiar et al., Synthetic Approaches to Regioregular Unsymmetrical Dialkoxy-Substituted Poly(1,4-phenylene ethynylene)s, *Macromolecules* (Dec. 15, 2008), 42(1):43-51.

Nanos et al., Poly(alkylbithiazoles): A New Class of Variable-Bandgap, Conjugated Polymer, *Chem. Mater.* (Dec. 1995), 7(12):2232-2234 (Abstract).

Pang et al., A Processible Poly(phenyleneethynylene) with Strong Photoluminescence: Synthesis and Characterization of Poly[(m-phenyleneethynylene)-*alt*- (p-phenyleneethynylene)], *Macromolecules* (Aug. 27, 1998), 31(19):6730-6732 (Abstract).

Pasquini et al., One-Step Synthesis of Low Molecular Weight Poly(p-phenyleneethynylenevinylene)s via Polyaddition of Aromatic Diynes by Catalysis of the [Ru(p-cymene)Cl$_2$]$_2$/AcOH System, *J. Org. Chem.* (Apr. 15, 2008), 73(10):3892-3899 (Abstract).

Pei et al., Efficient Photoluminescence and Electroluminescence from a Soluble Polyfluorene, *J. Am. Chem. Soc.* (Aug. 7, 1996), 118(31):7416-7417 (Abstract).

Richter et al., A surprising observation about Mitsunobu reactions in solid phase synthesis, *Tetrahedron Letters* (Jul. 4, 1994), 35(27):4705-4706 (Abstract).

Scherf, Ladder-type materials, *J. Mater. Chem.* (1999), 9:1853-1864 (Abstract).

Swager, The Molecular Wire Approach to Sensory Signal Amplification, *Acc. Chem. Res.* (Apr. 4, 1998), 31(5):201-207 (Abstract).

Wadsworth et al., The Utility of Phosphonate Carbanions in Olefin Synthesis, *J. Am. Chem. Soc.* (Apr. 1961), 83(7):1733-1738 (Abstract).

Wang et al., Coupling of FRET and Photoinduced Electron Transfer in Regioregular Silylene-Spaced Energy Donor-Acceptor-Electron Donor Copolymers, *Macromolecules* (Mar. 25, 2008), 41:2762-2770 (Abstract).

Wang et al., Synthesis, Properties, and Tunable Supramolecular Architecture of Regioregular Poly(3-alkylthiophene)s with Alternating Alkyl and Semifluoroalkyl Substituents, *Macromolecules* (Jun. 18, 2008), 41(14):5156-5165 (Abstract).

Weder et al., Highly polarized luminescence from oriented conjugated polymer/polyethylene blend films, *Adv. Mater.* (Oct. 29, 2004), 9(13):1035-1039 (Abstract).

Woody et al., Synthesis and Properties of Amphiphilic Poly(1,4-Phenylene Ethynylene)s Bearing Alkyl and Semifluoroalkyl Substituents, *Macromolecules* (Sep. 10, 2009), 42(21):8102-8111 (Abstract).

Xiao et al., Electrochemical Gate-Controlled Conductance of Single Oligo (phenylene ethynylene)s, *J. Am. Chem. Soc.* (Jun. 1, 2005), 127(25):9235-9240 (Abstract).

Yang et al., Fluorescent Porous Polymer Films as TNT Chemosensors: Electronic and Structural Effects, *J. Am. Chem. Soc.* (Nov. 11, 1998), 120(46):11864-11873 (Abstract).

\* cited by examiner

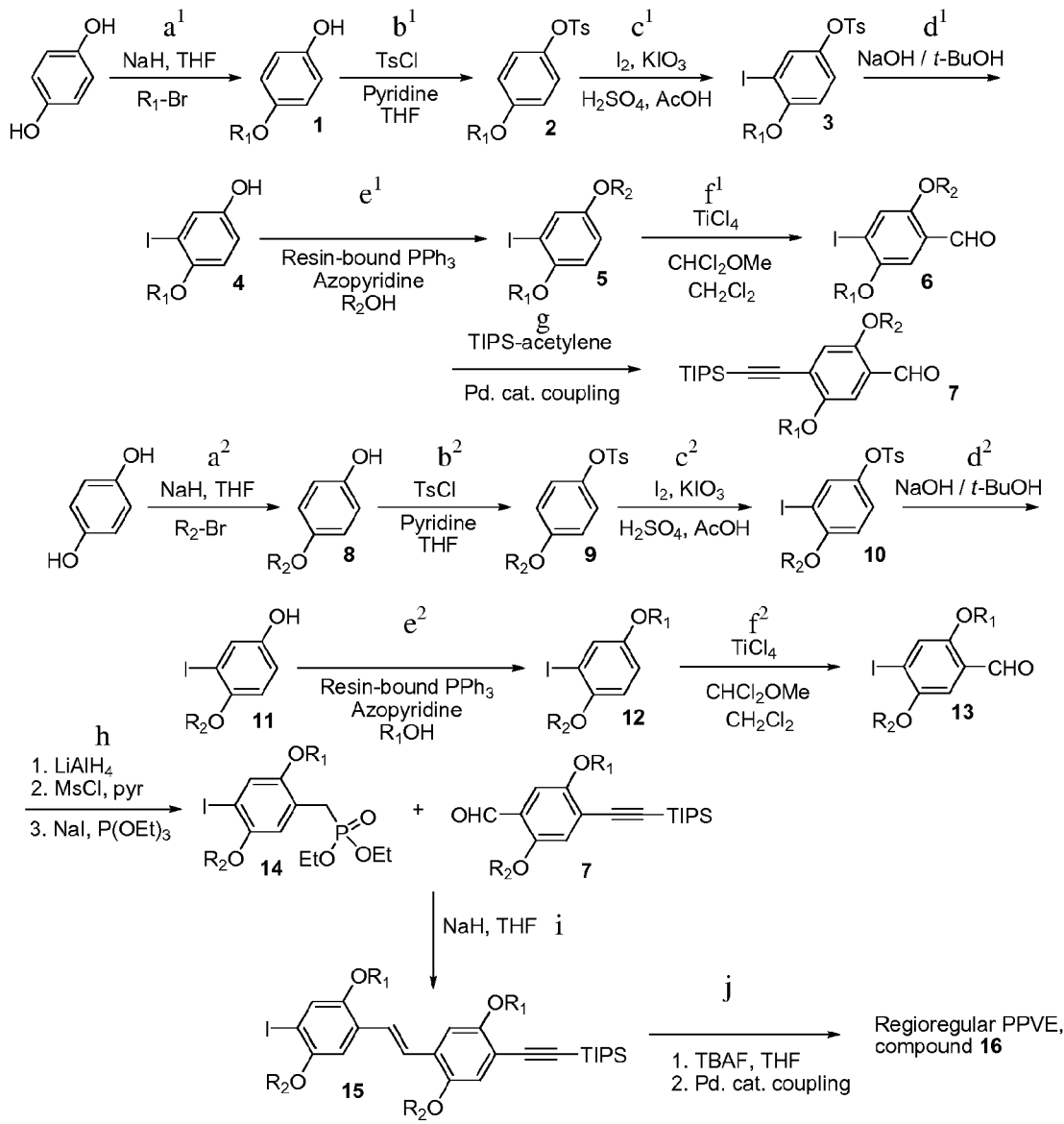

REGIOREGULAR COPOLYMERS AND METHODS FOR MAKING SAME

CROSS-REFERENCE TO RELATED APPLICATIONS

The present application is a continuation application filing under 35 U.S.C. §120 of U.S. patent application Ser. No. 13/811,758, filed Jan. 23, 2013, now U.S. Pat. No. 8,937,148, entitled "Regioregular Copolymers and Methods for Making Same," which in turn claims the benefit of and priority to U.S. national stage filing under 35 U.S.C. §371 of International Application No. PCT/US2012/054147, filed Sep. 7, 2012 and entitled "Regioregular Copolymers and Methods for Making Same," the disclosure of which is incorporated by reference in its entirety and for all purposes.

BACKGROUND

The classes of polymers known as poly(p-phenyleneethynylene)s, or PPEs, and poly(p-phenylenevinylene)s, or PPVs, have found uses as active layers in light-emitting diodes, "plastic lasers," light emitting-electrochemical cells, thin film transistors, and chemical sensors. Hybrid polyphenylenevinylene-ethynylenes copolymers, or "PPVEs," having strictly alternating PPE and PPV monomeric units combine the physical (phase, thermal) behaviour of the PPEs/PPVs with a new class of optical properties, including enhanced electron affinity. This makes PPVEs incredibly promising candidates for use in transistors and other solid-state electronic devices. Their unique electronics can be easily tuned via the side chains, while retaining the well-understood solid-state phase behaviour, X-ray diffraction, and the like of the PPEs. Such PPVE polymers have been used for their charge carrier mobility, especially in anthracene-PPVE copolymers, electroluminescent properties, photovoltaic properties for use in solar cells, and as the active component in thin film field effect transistors.

Work on poly(thiophene)s has shown that the identity and relative position of side chains along a conjugated polymer backbone has a large impact on the properties of the resulting polymer. Normal polymerization methods incorporate all possible combinations into the backbone, producing an inherently regiorandom polymer. There are steric and (in some cases) electronic "clashes" between side chains which "point" towards each other, twisting the backbone out of planarity with corresponding effects on the effective conjugation length and overall polymer crystallinity. This is of great importance, not only for the poly(thiophene)s but for any rigid-rod conjugated polymer that experiences a similar occurrence.

Regioregular materials have higher crystallinity, red-shifted absorptions in the optical region, a greater conductivity, and (usually) a smaller band-gap compared to the regiorandom versions of the same polymer. This has direct and powerful implications on the use of these materials for electronic applications. These effects have been studied in poly(1,4-phenylenevinylene)s and poly(1,4-phenyleneethynylene)s, but not for PPVEs due primarily to a lack of a valid synthetic route to regioregular PPVEs.

SUMMARY

Embodiments of the invention are generally directed to methods for preparing regioregular copolymers, monomeric units useful in such methods, and methods for preparing these monomeric units. For example, some embodiments include methods for making regioregular aryl ethynyl-aryl vinyl copolymers that include a compound of Formula IV:

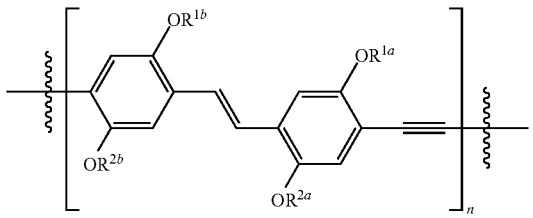

IV wherein each $R^{1a}$, $R^{1b}$, $R^{2a}$, and $R^{2b}$, independently, is $C_1$-$C_{20}$ alkyl, $C_2$-$C_{20}$ alkene, $C_2$-$C_{20}$ alkyne, or alkylene glycol and n is an integer of 2 or more.

Other embodiments include compounds having the general Formula I:

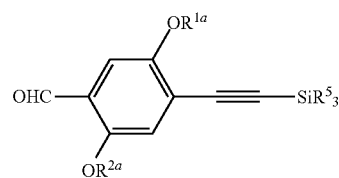

I wherein each $R^{1a}$ and $R^{2a}$ is, independently, $C_1$-$C_{20}$ alkyl, $C_2$-$C_{20}$ alkene, $C_2$-$C_{20}$ alkyne, or alkylene glycol and each $R^5$ is, independently, $C_1$-$C_{20}$ alkyl. Further embodiments include methods for making the compounds of Formula I, and methods that use such compounds for the production of regioregular aryl ethynyl-aryl vinyl copolymers.

Still other embodiments include compounds having the general Formula II:

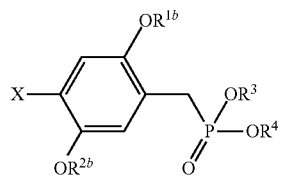

II wherein each $R^{1b}$ and $R^{2b}$ is, independently, $C_1$-$C_{20}$ alkyl, $C_2$-$C_{20}$ alkene, $C_2$-$C_{20}$ alkyne, or alkylene glycol; each $R^3$ and $R^4$ is, independently, $C_1$-$C_{20}$ alkyl; and X is hydroxide, alkoxide, astatine, iodine, bromine, chlorine, or fluorine, triflate ($CF_3SO_3^-$), mesylate ($CH_3SO_3^-$), tosylate ($CH_3C_6H_4SO_2^-$), or besylate ($C_6H_5SO_3^-$). Further embodiments include methods for making the compounds of Formula II, and methods that use such compounds for the production of regioregular copolymers.

Yet other embodiments are directed to compounds having the general Formula III:

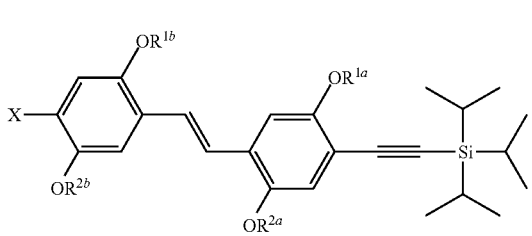

III wherein each $R^{1a}$, $R^{1b}$, $R^{2a}$, and $R^{2b}$ is, independently, $C_1$-$C_{20}$ alkyl, $C_2$-$C_{20}$ alkene, $C_2$-$C_{20}$ alkyne, or alkylene glycol; and X is hydroxide, alkoxide, astatine, iodine, bromine, chlorine, or fluorine, triflate ($CF_3SO_3^-$), mesylate ($CH_3SO_3^-$), tosylate ($CH_3C_6H_4SO_2^-$), or besylate ($C_6H_5SO_3^-$). Further embodiments include methods for making the compounds of Formula III, and methods that use such compounds for the production of regioregular copolymers. Additional embodiments include methods for making compounds of general Formula III from compounds of general Formulae I and II.

BRIEF DESCRIPTION OF THE FIGURES

In the following detailed description, reference is made to the accompanying drawings, which form a part hereof. In the drawings, similar symbols typically identify similar components unless context dictates otherwise. The illustrative embodiments described in the detailed description, drawings, and claims are not meant to be limiting. Other embodiments may be utilized and other changes may be made, without departing from the spirit or scope of the subject matter presented herein. It will be readily understood that the aspects of the present disclosure, as generally described herein and illustrated in the Figures, can be arranged, substituted, combined, separated, and designed in a wide variety of different configurations, all of which are explicitly contemplated herein.

FIG. 1 is a schematic of a chemical synthesis corresponding to the synthesis scheme defined herein.

DETAILED DESCRIPTION

Various embodiments are directed to monomeric units that can be used in the production of polymers as well as methods for making these monomers. Further embodiments are directed to polymers created using these monomeric units and methods for making such polymers. The monomeric units, or monomers, can be incorporated into any polymer or type of polymer known in the art including various thermoplastic and thermoset resins, and in particular embodiments, the monomers of the invention can be incorporated into regioregular copolymers.

The monomeric units of various embodiments generally include at least one aromatic moiety. For example, in some embodiments, the monomeric unit may be a silylalkynyl dialkoxyl arylaldehyde such as, but not limited to, a compound of general Formula I:

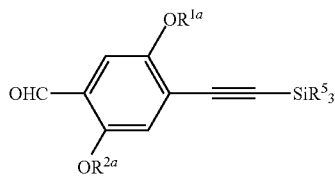

I where each $R^{1a}$ and $R^{2a}$ can, independently, be $C_1$-$C_{20}$ alkyl, $C_2$-$C_{20}$ alkene, $C_2$-$C_{20}$ alkyne, or alkylene glycol and each $R^5$ can be $C_1$-$C_{20}$ alkyl. In other embodiments, the monomeric unit may be a X-substituted dialkoxyl arylphosphonate such as, but not limited to, a compound of general Formula II:

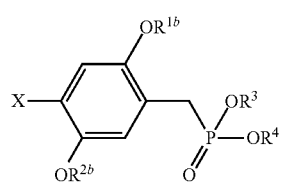

II where each $R^{1b}$ and $R^{2b}$ is, independently, $C_1$-$C_{20}$ alkyl, $C_2$-$C_{20}$ alkene, $C_2$-$C_{20}$ alkyne, or alkylene glycol; each $R^3$ and $R^4$ is, independently, $C_1$-$C_{20}$ alkyl; and X can be, for example, hydroxide, alkoxide, astatine, iodine, bromine, chlorine, or fluorine, triflate ($CF_3SO_3^-$), mesylate ($CH_3SO_3^-$), tosylate ($CH_3C_6H_4SO_2^-$), or besylate ($C_6H_5SO_3^-$). In still other embodiments, the monomeric unit may be a X-substituted silylalkynyl diarylethene such as, but not limited to, a compound of general Formula III:

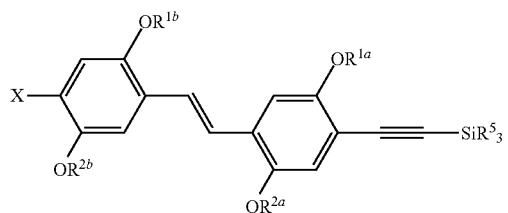

III where each $R^{1a}$, $R^{1b}$, $R^{2a}$, and $R^{2b}$ can, independently, be $C_1$-$C_{20}$ alkyl, $C_2$-$C_{20}$ alkene, $C_2$-$C_{20}$ alkyne, or alkylene glycol, $R^5$ can be $C_1$-$C_{20}$ alkyl, and X can be, for example, hydroxide, alkoxide, astatine, iodine, bromine, chlorine, or fluorine, triflate ($CF_3SO_3^-$), mesylate ($CH_3SO_3^-$), tosylate ($CH_3C_6H_4SO_2^-$), or besylate ($C_6H_5SO_3^-$). In each of the embodiments, described above, $R^{1a}$ and $R^{1b}$ can be the same, $R^{2a}$ and $R^{2b}$ can be the same, or $R^{1a}$ and $R^{1b}$ can be the same and $R^{2a}$ and $R^{2b}$ can be the same, and in some embodiments, $R^{1a}$, $R^{1b}$, $R^{2a}$, and $R^{2b}$ can each be different, or various combinations of $R^{1a}$, $R^{1b}$, $R^{2a}$, and $R^{2b}$ can be the same or different.

Without wishing to be bound by theory, the leaving groups X, e.g. hydroxide, alkoxide, astatine, iodine, bromine, chlorine, or fluorine, triflate ($CF_3SO_3^-$), mesylate ($CH_3SO_3^-$), tosylate ($CH_3C_6H_4SO_2^-$), or besylate ($C_6H_5SO_3^-$), phosphonate ($P(O)OR^3OR^4$), aldehyde (CHO), and silyl ($\equiv C(SiR_5)_3$) groups associated with the monomeric units exemplified above may allow these monomeric units to be particularly useful for any number of polymerization reactions. Moreover, the arrangement of these leaving groups provides a means for controlling the arrangement of these monomeric units. For example, in certain embodiments, the monomeric units described above, or other compounds having the leaving groups described above may be used in the preparation of regiospecific or regioregular polymers in reactions that are regioselective. A "regioselective reaction" is a chemical reaction in which one direction of bond making or breaking occurs preferentially over all other possible directions. The term "regiospecific" or "regiospecific reaction" as used herein refers to a polymerization reaction that is 100% or nearly 100% regioselective, resulting in a polymer that is exclusively or nearly exclusively composed of one of several possible isomeric products. Generally, regiospecific is defined as a reaction that results in regioselectivity within the limit of detection. For $^1$H NMR, the current standard method, about 95% to about 100%, about 97% to about 100%, about 98% to about 100%, or about 99% to about 100% of the bonds in a regiospecific polymer will be of one isomeric product. The isomeric products of regiospecific reactions are referred to as "regioregular polymers."

In some embodiments, the monomeric units may be used in regioselective or regiospecific reactions that are intended to result in regioregular polymers. For example, particular embodiments are directed to a method for preparing regioregular aryl ethynyl-aryl vinyl copolymers. In general, such methods may include the steps of providing a silylalkynyl dialkoxyl arylaldehyde and a X-substituted dialkoxyl arylphosphonate and contacting the silylalkynyl dialkoxyl arylaldehyde and the X-substituted dialkoxyl arylphosphonate under conditions that provide for coupling of the silylalkynyl dialkoxyl arylaldehyde and the X-substituted dialkoxyl arylphosphonate to provide a X-substituted silylalkynyl diarylethene. In particular embodiments, the silylalkynyl dialkoxyl arylaldehyde may be a compound of Formula I:

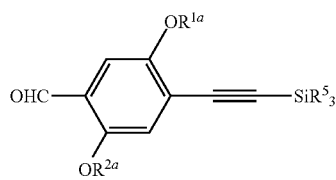

I where each $R^{1a}$ and $R^{2a}$ can, independently, be $C_1$-$C_{20}$ alkyl, $C_2$-$C_{20}$ alkene, or $C_2$-$C_{20}$ alkyne and each $R^5$ can be $C_1$-$C_{20}$ alkyl, and in some embodiments, the X-substituted dialkoxyl arylphosphonate comprises a compound of Formula II:

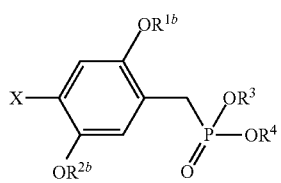

II where each $R^{1b}$ and $R^{2b}$ can, independently, be $C_1$-$C_{20}$ alkyl, $C_2$-$C_{20}$ alkene, $C_2$-$C_{20}$ alkyne, or alkylene glycol, each $R^3$ and $R^4$ can, independently, be $C_1$-$C_{20}$ alkyl, and X can be, for example, hydroxide, alkoxide, astatine, iodine, bromine, chlorine, or fluorine, triflate ($CF_3SO_3^-$), mesylate ($CH_3SO_3^-$), tosylate ($CH_3C_6H_4SO_2^-$), or besylate ($C_6H_5SO_3^-$). In certain embodiments, $R^{1a}$ and $R^{1b}$ can be the same and $R^{2a}$ and $R^{2b}$ can be the same. In particular embodiments, contacting the silylalkynyl dialkoxyl arylaldehyde and the X-substituted dialkoxyl arylphosphonate under conditions that provide for coupling of the silylalkynyl dialkoxyl arylaldehyde and the X-substituted dialkoxyl arylphosphonate may include a Horner-Wadsworth-Emmons coupling. The X-substituted dialkoxyl arylphosphonate may be of any formula and, in some embodiments, may be a compound of Formula III:

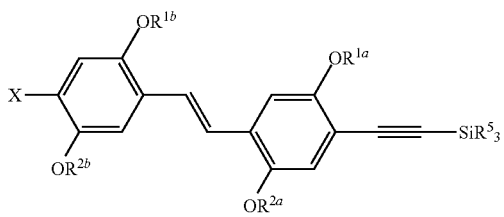

III where each $R^{1a}$, $R^{1b}$, $R^{2a}$, and $R^{2b}$ can, independently, be $C_1$-$C_{20}$ alkyl, $C_2$-$C_{20}$ alkene, $C_2$-$C_{20}$ alkyne, or alkylene glycol, $R^5$ can be $C_1$-$C_{20}$ alkyl, and X can be, for example, hydroxide, alkoxide, astatine, iodine, bromine, chlorine, or fluorine, triflate ($CF_3SO_3^-$), mesylate ($CH_3SO_3^-$), tosylate ($CH_3C_6H_4SO_2^-$), or besylate ($C_6H_5SO_3^-$).

In some embodiments, such methods may further include the steps of placing the X-substituted silylalkynyl diarylethene under conditions that allow the silyl moiety to be removed from the X-substituted silylalkynyl diarylethene to provide a X-substituted alkynyl diarylethene and placing the X-substituted alkynyl diarylethene under conditions that allow X-substituted alkynyl diarylethenes to be coupled to provide the regioregular aryl ethynyl-aryl vinyl copolymer. In particular embodiments, the coupling reaction resulting from placing the X-substituted alkynyl diarylethene under conditions that allow the X-substituted alkynyl diarylethenes to be coupled may be a Sonogashira coupling.

In embodiments, such as those described above, the resulting regioregular copolymer may be a compound of Formula IV:

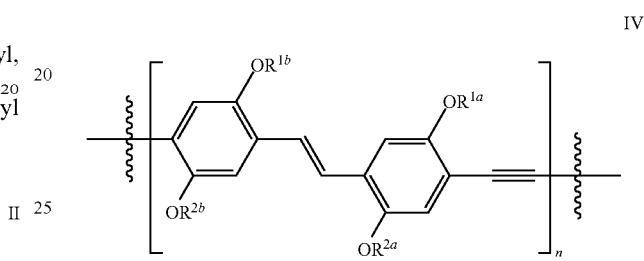

IV where each $R^{1a}$, $R^{1b}$, $R^{2a}$, and $R^{2b}$ can, independently, be $C_1$-$C_{20}$ alkyl, $C_2$-$C_{20}$ alkene, $C_2$-$C_{20}$ alkyne, or alkylene glycol, and n can be an integer from 2 or more, or in some embodiments, n may be an integer from 2 to 100. In certain embodiments, $R^{1a}$ and $R^{1b}$ may be the same and $R^{2a}$ and $R^{2b}$ may be the same, and in particular embodiments, the copolymer of Formula IV can be regioregular.

The method described above may have any number of additional steps, and such additional steps may be carried out in any order. For ease of description, FIG. 1 provides a reaction scheme for the synthesis of various regioregular copolymers encompassed by the invention. Intermediate compounds formed during the synthesis are numbered and individual steps in the synthesis method are identified using letters. As indicated by the superscripts, steps a-f are carried out in the preparation of both monomeric units corresponding to Formulae I and II described above, which are identified in the reaction scheme of FIG. 1 as compounds 7 and 14 respectively.

In FIG. 1, synthesis of the regioregular aryl ethynyl-aryl vinyl copolymers begins in step $a^1$, $a^2$ by providing a para-substituted arene 0, which is exemplified by hydroquinone, and a halogenated $C_2$-$C_{20}$ alkyl, $C_2$-$C_{20}$ alkene, $C_2$-$C_{20}$ alkyne, or alkylene glycol. These components are combined or "contacted" under conditions that allow the para-substituted arene 0 and the halogenated $C_2$-$C_{20}$ alkyl, $C_2$-$C_{20}$ alkene, $C_2$-$C_{20}$ alkyne, or alkylene glycol to react to provide a monoalkoxyl para-substituted arene 1. In some exemplary embodiments, the para-substituted arene may be hydroquinone, and in certain embodiments, the monoalkoxyl para-substituted arene 1 produced by this step may be a 4-alkoxyphenol. In particular embodiments, the halogenated $C_2$-$C_{20}$ alkyl, $C_2$-$C_{20}$ alkene, or $C_2$-$C_{20}$ alkyne used in step $a^1$ may be different from the halogenated $C_2$-$C_{20}$ alkyl, $C_2$-$C_{20}$ alkene, or $C_2$-$C_{20}$ alkyne used in step $a^2$ such that $R^{1a}$ of intermediate 1 may be different from $R^{2b}$ of intermediate 8. In other embodiments, the halogenated $C_2$-$C_{20}$ alkyl, $C_2$-$C_{20}$ alkene, $C_2$-$C_{20}$ alkyne, or alkylene glycol used in step $a^1$, $a^2$ may be the same such that intermediates 1 and 8 will be the same.

Steps $a^1$-$f^1$ and $a^2$-$f^2$ are generally carried out separately; however, in certain embodiments in which $R^{1a}$ and $R^{2b}$ are the same, steps $a^1$-$f^1$ and $a^2$-$f^2$ may be carried out simultaneously in the same reaction vessel.

Attachment of one side chain to the para-substituted arene 0 is generally achieved by nucleophilic substitution ($S_N2$), which typically produces about 60% to about 70% yield of the monoalkoxyl para-substituted hydroxyarene 1 product. Without wishing to be bound by theory, based on the different solubilities of para-substituted arene 0, the monoalkoxyl para-substituted hydroxyarene 1, and di-substituted by-products, the monoalkoxyl para-substituted hydroxyarene 1 can be easily purified by recrystallization. The size and nature of $R^1$ and/or $R^2$ can vary among embodiments, and may depend on the intended end use of the polymer. In embodiments in which $R^1$ and/or $R^2$ are long alkyl chains, recrystallization may result in a white solid.

In step $b^1$, $b^2$, a protecting group may be introduced onto the monoalkoxyl para-substituted hydroxyarene 1, 8, at the remaining hydroxyl in a step that includes contacting a protecting group containing compound and the monoalkoxyl para-substituted hydroxyarene 1, 8 under conditions that allow the protecting group containing compound and the monoalkoxyl para-substituted hydroxyarene 1, 8, to react to provide the protected monoalkoxyl para-substituted arene 2, 9. The protecting group containing compound may be any known protecting group containing compound, and in some embodiments, the protecting group may be bulky and/or electron withdrawing. For example, in various embodiments, the protecting group containing compound may be acetyl, benzoyl, benzyl, β-methoxyethoxymethyl ether, dimethoxytrityl, [bis-(4-methoxyphenyl)phenylmethyl], methoxymethyl ether, methoxytrityl [(4-methoxyphenyl)diphenylmethyl], p-methoxybenzyl ether, methylthiomethyl ether, pivaloyl, tetrahydropyranyl, trityl triphenylmethyl, silyl ether, trimethylsilyl ether, tert-butyldimethylsilyl ether, tri-iso-propylsilyloxymethyl ether, tri-iso-propylsilyl ether, ethoxyethyl ether, carbobenzyloxy, p-methoxybenzyl carbonyl, tert-butyloxycarbonyl, 9-fluorenylmethyloxycarbonyl, carbamate, p-methoxybenzyl, 3,4-dimethoxybenzyl, p-methoxyphenyl, tosyl, sulfonamide, and the like and combinations thereof. In particular embodiments, the protecting group may be a tosyl, and in certain embodiments, protected monoalkoxyl para-substituted arene 2, 9, may be 4-(alkoxy)phenyl 4-protecting group, such as the tosylate (Ts) containing compound, 4-(alkoxy)phenyl 4-methylbenzensulfonate, in FIG. 1. In embodiments, in which the protecting group is a tosylate group, the addition of the protecting group may be carried out by combining the monoalkoxyl para-substituted arene 1, 8, with tosyl chloride (TsCl) in pyridine at room temperature. Without wishing to be bound by theory, a tosylate protecting group is stable to acid, readily cleaved by base, but also presents a steric barrier towards electrophilic aromatic substitution at the a-substituents on the benzene ring of the monoalkoxyl para-substituted arene 1, 8.

In various embodiments, a leaving group (X) may be introduced onto the arene of the monoalkoxyl para-substituted arene 2, 9, at a carbon adjacent to the alkoxy substituent, step $c^1$, $c^2$. In various embodiments, the leaving group X can be, for example, hydroxide, alkoxide, astatine, iodine, bromine, chlorine, or fluorine, triflate ($CF_3SO_3^-$), mesylate ($CH_3SO_3^-$), tosylate ($CH_3C_6H_4SO_2^-$), or besylate ($C_6H_5SO_3^-$). In exemplary embodiments, the leaving group (X) may consist of iodine. Thus, the method of embodiments may include the step of placing the protected monoalkoxyl arene 2, 9, under conditions that allow the addition of a leaving group (X) to the protected monoalkoxyl arene 2, 9, to provide the protected X-substituted monoalkoxyl arene 3, 10. In certain embodiments, the protected X-substituted monoalkoxyl arene 3, 10, may be 3-halogen 4-alkoxyphenyl 1-protecting group, and in some embodiments, the protected X-substituted monoalkoxyl arene 3, 10, may be 3-iodo-4-(alkoxy)phenyl 1-methylbenzensulfonate, as illustrated in FIG. 1. Without wishing to be bound by theory, the presence of the protecting group opposite the alkoxyl group, i.e., at a para position, may reduce or eliminate the possibility of a leaving group (X) being introduced onto a carbon adjacent to the protecting group. In some embodiments, introducing a leaving group (X) onto the monoalkoxyl arene 2, 9, can be carried out by oxidative iodination in acidic medium which yields the desired monoiodinated monoalkoxyl arene 3, 10 in good yield.

In various embodiments, the protecting group may be removed after the addition of a leaving group (X) has been carried out. For example, in some embodiments, the method may include the step of placing the protected X-substituted monoalkoxyl para-substituted arene 3, 10, under conditions that allow a protecting group to be removed from the protected X-substituted monoalkoxyl arene 3, 10, to provide the unprotected X-substituted monoalkoxyl hydroxyarene 4, 11. In particular embodiments where the leaving group (X) consists of iodine, a tosylate group may be removed by a mixture of aqueous sodium hydroxide (NaOH) and t-butanol at reflux, and acidic workup can yield free iodophenol.

A second alkyl, alkene, or alkyne $R^{2a}$, $R^{1b}$ can then be introduced onto the hydroxyl remaining after the protecting group has been removed. In some embodiments, the method may include the step $e^1$, $e^2$ of contacting a hydroxylated $C_1$-$C_{20}$ alkyl, $C_2$-$C_{20}$ alkene, $C_2$-$C_{20}$ alkyne, or alkylene glycol, and the unprotected X-substituted monoalkoxyl hydroxyarene 4, 11, under conditions that allow the hydroxylated $C_1$-$C_{20}$ alkyl, $C_2$-$C_{20}$ alkene, $C_2$-$C_{20}$ alkyne, or alkylene glycol and the unprotected X-substituted monoalkoxyl hydroxyarene 4, 11, to react to provide the unprotected X-substituted dialkoxyl arene 5, 12. In various embodiments, the alkyl, alkene, alkyne, or alkylene glycol $R^{2a}$, $R^{1b}$ introduced in step $e^1$, $e^2$ may be the same as the alkyl, alkene, alkyne, or alkylene glycol $R^{1a}$, $R^{2b}$ introduced onto the para-substituted arene 0 in step $a^1$, $a^2$. In certain embodiments, the alkyl, alkene, alkyne, or alkylene glycol $R^{2a}$ introduced in step $e^1$ may be the same alkyl, alkene, or alkyne $R^{2b}$ introduced in step $a^2$, and the alkyl, alkene, alkyne, or alkylene glycol $R^{1b}$ introduced in step $e^2$ may be the same alkyl, alkene, alkyne, or alkylene glycol $R^{1a}$ introduced in step $a^1$. Thus, in some embodiments, the hydroxylated $C_2$-$C_{20}$ alkyl, $C_2$-$C_{20}$ alkene, $C_2$-$C_{20}$ alkyne, or alkylene glycol and the halogenated $C_2$-$C_{20}$ alkyl, $C_2$-$C_{20}$ alkene, $C_2$-$C_{20}$ alkyne, or alkylene glycol may include different $C_1$-$C_{20}$ alkyl, $C_2$-$C_{20}$ alkene, $C_2$-$C_{20}$ alkyne, or alkylene glycol moieties. In particular embodiments, the step of contacting in steps $e^1$ and $e^2$ may include a Mitsunobu coupling, and in some embodiments, the Mitsunobu coupling can be carried out using resin bound triphenylphosphine ($PPh_3$). A Mitsunobu coupling is then used which may utilize modified conditions, including resin-bound $PPh_3$ (to enable easy purification of the coupled product/regeneration of the resin) as well as azopyridine instead of diethyl azodicarboxylate (DEAD), which can be regenerated and reused. In particular embodiments, the second side chain attached in this step can be non-identical to $R^1$ and can be tailored to meet the final demands of the polymer.

The methods of various embodiments may further include the step of introducing an aldehyde-containing substituent onto the unprotected X-substituted dialkoxyl arene 5, 12. Such steps can be carried out by contacting a $C_1$-$C_6$ alkoxy $C_1$-$C_6$ dihaloalkyl and the unprotected X-substituted dialkoxyl arene 5, 12 under conditions that allow the $C_1$-$C_6$ alkoxy $C_1$-$C_6$ dihaloalkyl and the unprotected X-substituted dialkoxyl arene 5, 12 to react to provide the X-substituted dialkoxyl arylaldehyde 6, 13. In certain embodiments, the X-substituted dialkoxyl arylaldehyde 6, 13 may be a compound of Formula V:

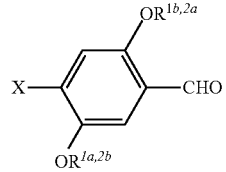

where each $R^{1a}$, $R^{1b}$, $R^{2a}$, and $R^{2b}$ can, independently, be $C_1$-$C_{20}$ alkyl, $C_2$-$C_{20}$ alkene, $C_2$-$C_{20}$ alkyne, or alkylene glycol; and X can be, for example, hydroxide, alkoxide, astatine, iodine, bromine, chlorine, or fluorine, triflate ($CF_3SO_3^-$), mesylate ($CH_3SO_3^-$), tosylate ($CH_3C_6H_4SO_2^-$), or besylate ($C_6H_5SO_3^-$). Without wishing to be bound by theory, the directing effects of the $R^{2a}$ or $R^{1b}$ and $R^{1a}$, or $R^{2b}$ and the leaving group (X) on the benzene cause the aldehyde (CHO) to be positioned opposite, i.e., para, to the leaving group (X) under various reaction conditions. For example, in particular embodiments, when the X-substituted dialkoxyl arene 5, 12 may be exposed to a mixture of $TiCl_4/CHCl_2OCH_3$ dissolved in dichloromethane ($CH_2Cl_2$) at low temperatures (−10° C., ice-salt bath) to provide the X-substituted dialkoxyl arylaldehyde 6, 13 having the aldehyde in the proper position.

As discussed above, the synthetic route for silylalkynyl dialkoxyl arylaldehyde 7 monomer and the X-substituted dialkoxyl arylphosphonate 14 are similar. However, in certain embodiments, the side chain $R^{1a,2b}$ may be first attached to the para-substituted arene 0 first instead of $R^{2a,1b}$ to ensure that in the final monomer, similar side chains are arranged in the proper orientation with respect to each other and do not become mismatched. This provides the regioregular polymer. Thus steps leading up to intermediate 6 are the same as the steps leading to intermediate 13, with the exception that now the placement of the two side chains are switched.

The preparation of the silyl-containing monomer of Formula I, intermediate 7 in FIG. 1, may proceed by introducing a silyl containing group onto the X-substituted dialkoxyl arylaldehyde 6, step g. For example, in some embodiments, the method may include contacting a silyl-alkynyl and the X-substituted dialkoxyl arylaldehyde 6 under conditions that allow the silyl-alkynyl and X-substituted dialkoxyl arylaldehyde 6 to react to provide the silylalkynyl dialkoxyl arylaldehyde 7. The silyl-alkynyl may be any silyl alkynyl group known in the art including, but not limited to, trimethylsilyl acetylene, tert-butyldimethylsilyl acetylene, tri-iso-propylsilyloxymethyl acetylene, or tri-iso-propylsilyl acetylene, and in certain embodiments, the silyl-alkynyl may be tri-iso-propylsilyl acetylene, i.e., TIPS, as exemplified in FIG. 1. Step g, may result in a compound of Formula I:

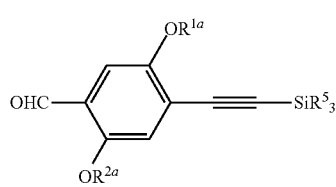

where each $R^{1a}$ and $R^{2a}$ can, independently, be $C_1$-$C_{20}$ alkyl, $C_2$-$C_{20}$ alkene, $C_2$-$C_{20}$ alkyne, or alkylene glycol and each $R^5$ can be $C_1$-$C_{20}$ alkyl. In particular embodiments the monomeric unit 7 resulting from step g may be a compound of general Formula Ia:

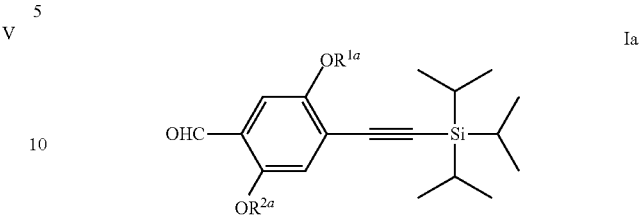

where $R^{1a}$ and $R^{2a}$ can, independently, be $C_1$-$C_{20}$ alkyl, $C_2$-$C_{20}$ alkene, $C_2$-$C_{20}$ alkyne, or alkylene glycol. In particular embodiments, the X-substituted dialkoxyl arylaldehyde 6 can be coupled to one equivalent of silyl containing compound such as TIPS-acetylene (TIPS=tri-iso-propyl silyl) under palladium-catalyzed coupling conditions to produce a protected alkyne, silylalkynyl dialkoxyl arylaldehyde 7. The reaction proceeds quantitatively, and the TIPS-alkyne group is stable to a wide variety of reaction conditions and can be easily removed to give the bare alkyne.

The phosphonate containing monomer of Formula II, intermediate 14 in FIG. 1, can be produced by introducing a phosphonate group into the X-substituted dialkoxyl arylaldehyde 13, step h. In some embodiments, the method may include the step of contacting a phosphonate containing compound and the X-substituted dialkoxyl arylaldehyde 13 under conditions that allow the phosphonate containing compound and the X-substituted dialkoxyl arylaldehyde 13 to react to provide the X-substituted dialkoxyl arylphosphonate monomer 14. Step h may generally result in a X-substituted dialkoxyl arylphosphonate 14 having a structure of Formula II:

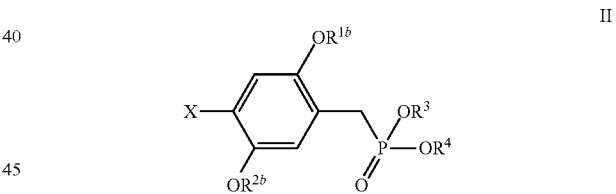

where each $R^{1b}$ and $R^{2b}$ can, independently, be $C_1$-$C_{20}$ alkyl, $C_2$-$C_{20}$ alkene, $C_2$-$C_{20}$ alkyne, or alkylene glycol, each $R^3$ and $R^4$ can, independently, be $C_1$-$C_{20}$ alkyl, and X can be, for example, hydroxide, alkoxide, astatine, iodine, bromine, chlorine, or fluorine, triflate ($CF_3SO_3^-$), mesylate ($CH_3SO_3^-$), tosylate ($CH_3C_6H_4SO_2^-$), or besylate ($C_6H_5SO_3^-$).

In particular embodiments, contacting the phosphonate-containing compound and the X-substituted dialkoxyl arylaldehyde 13 may include various additional steps such as, for example, placing the X-substituted dialkoxyl arylaldehyde 13 under conditions that allow the X-substituted dialkoxyl arylaldehyde 13 to be reduced to provide a X-substituted dialkoxyl arylmethanol; combining the X-substituted dialkoxyl arylmethanol with a leaving group containing compound; contacting the leaving group containing compound with the X-substituted dialkoxyl arylmethanol under conditions that allow the leaving group containing compound with the X-substituted dialkoxyl arylmethanol to provide a X-substituted dialkoxyl arylmethyl-leaving group; contacting the X-substituted dialkoxyl arylmethyl-leaving group with a phosphite containing compound under conditions that allow the X-substituted dialkoxyl arylmethyl-leaving group with a phosphite containing compound to react; and allowing an Arbuzov rearrangement to occur to provide the X-substituted dialkoxyl arylphosphonate 14 monomer. In various such embodiments, the leaving group can be, for example, hydroxide, alkoxide, astatine, iodine, bromine, chlorine, or fluorine, triflate ($CF_3SO_3^-$), tosylate ($CH_3C_6H_4SO_2^-$), or besylate ($C_6H_5SO_3^-$), or the like and combinations thereof, and in particular embodiments, the leaving group may be mesylate ($CH_3SO_3^-$). In some embodiments, the Arbuzov rearrangement can be carried out with a metal halide catalyst such as, for example, sodium iodide (NaI). This reaction can be done neat in triethylphosphite to drive the equilibrium towards formation of products and to reduce hazardous waste streams; residual leftover "solvent" can be vacuum stripped away and used for another batch.

Following preparation of the silyl containing monomeric unit, intermediate 7, and the phosphonate containing monomeric unit, intermediate 14, can be coupled to produce a X-substituted silylalkynyl diarylethene 15. In such embodiments, the method may include the steps of combining the silylalkynyl arylaldehyde 7 and the X-substituted arylphosphonate 14 and contacting the silylalkynyl arylaldehyde 7 and the X-substituted arylphosphonate 14 under conditions that allow the silylalkynyl arylaldehyde 7 and the X-substituted arylphosphonate 14 to react to create a X-substituted silylalkynyl diarylethene 15. In particular embodiments, the conditions under which the silylalkynyl arylaldehyde 7 and the X-substituted arylphosphonate 14 are combined to react comprises a Horner-Wadsworth-Emmons coupling. In some embodiments, the Horner-Wadsworth-Emmons coupling between intermediates 7 and 14 can be carried out using sodium hydride (NaH) in tetrahydrofuran (THF), and produces intermediate 15 in quantitative yield. Notably, the Horner-Wadsworth-Emmons coupling typically forms alkenes in exclusively the trans configuration.

Finally, a regioregular aryl ethynyl-aryl vinyl copolymer 16 can be produced by coupling X-substituted silylalkynyl diarylethenes 15. In certain embodiments, the coupling X-substituted silylalkynyl diarylethenes 15 may be carried out by placing the X-substituted silylalkynyl diarylethene 15 under conditions that allow the silyl to be removed to provide X-substituted alkynyl diarylethene 15 and contacting the X-substituted diarylethene alkynyl diarylethene 15 under conditions that allow the X-substituted diarylethene alkynyl diarylethene 15 to be coupled to provide a regioregular poly(aryl ethynyl)-poly(aryl vinyl) 16. In certain embodiments, the coupling of X-substituted alkynyl diarylethene diarylethene 15 can be carried out under conditions that allow the X-substituted diarylethene alkynyl diarylethene 15 to be coupled by a Sonogashira coupling. In particular embodiments, coupling X-substituted silylalkynyl diarylethenes 15 may be carried out with one equivalent of tetra-n-butyl ammonium fluoride (TBAF) in THF at room temperature. The fluoride ions produced under these conditions allow for the removal of the alkyne protecting group leaving a base alkyne and gives the monoethynyl monoiodo monomer. The Sonogashira coupling may generally avoid homo-coupled byproducts between two alkyne groups, which would introduce regiorandomness via diyne defects and results in the regioregular poly(aryl ethynyl)-poly(aryl vinyl) 16. The Sonogashira couplings can result in regioregular poly(aryl ethynyl)-poly(aryl vinyl) 16 having about 100 repeating units, which is well above the threshold of saturation for optical properties in these polymers.

The reaction described above allows for side chains having a wide variety of properties that will allow for the production of a wide variety of polymers having various characteristics of a fully regioregular polymer.

EXAMPLES

Example 1

Synthesis of 2-methoxy-5-ethoxy-4-((tri-iso-propylsilyl)ethynyl)benzaldehyde

Hydroquinone can be added to a solution of sodium hydride (NaH) dissolved in tetrahydrofuran (THF) and combined with ethyl bromide yielding para-ethoxyphenol. The para-ethoxyphenol can be extracted and added to a solution of tosyl chloride (TsCl) dissolved in pyridine and tetrahydrofuran (THF) at room temperature, yielding para-ethoxytosyloxybenzene. The para-ethoxytosyloxybenzene can be extracted and added to a solution of diatomic iodine ($I_2$) and potassium iodide trioxide ($KIO_3$) dissolved in sulfuric acid ($H_2SO_4$) and acetic acid ($CH_3COOH$) yielding 4-ethoxy-3-iodo-1-tosyloxybenzene. The 4-ethoxy-3-iodo-1-tosyloxybenzene is extracted and added to a solution of aqueous sodium hydroxide (NaOH) and tert-butanol, removing the tosylate protecting group and yielding 4-ethoxy-3-iodophenol. The 4-ethoxy-3-iodophenol can be extracted and exposed to resin-bound triphenylphosphine ($PPh_3$) in a solution of azopyridine and methanol ($CH_3OH$) in a salt bath at 0° C., yielding 4-ethoxy-3-iodomethoxybenzene. The 4-ethoxy-3-iodomethoxybenzene can be extracted and added to a solution of titanium tetrachloride ($TiCl_4$) and 1,1-dichlorodimethylether ($CHCl_2OCH_3$) dissolved in dichloromethane ($CH_2Cl_2$) in a salt bath at −10° C., yielding 2-methoxy-4-iodo-5-ethoxybenzaldehyde. The 2-methoxy-4-iodo-5-ethoxybenzaldehyde can be extracted and half of the yield can be added to tri-iso-propylsilylacetylene (TIPS-acetylene) in an amine solvent such as triethylamine, diethylamine, piperidine, or di-iso-propylethylamine. This mixture can be passed over a palladium (Pd) catalyst bed, yielding 2-methoxy-5-ethoxy-4-((tri-iso-propylsilyl)ethynyebenzaldehyde.

Example 2

Synthesis of diethyl 2-ethoxy-4-iodo-5-methoxybenzylphosphonate

Hydroquinone can be added to a solution of sodium hydride (NaH) dissolved in tetrahydrofuran (THF) and combined with methyl bromide yielding para-methoxyphenol. The para-methoxyphenol can be extracted and added to a solution of tosyl chloride (TsCl) dissolved in pyridine and tetrahydrofuran (THF) at room temperature, yielding para-methoxytosyloxybenzene. The para-methoxytosyloxybenzene can be extracted and added to a solution of diatomic iodine ($I_2$) and potassium iodide trioxide ($KIO_3$) dissolved in sulfuric acid ($H_2SO_4$) and acetic acid ($CH_3COOH$) yielding 4-methoxy-3-iodo-1-tosyloxybenzene. The 4-methoxy-3-iodo-1-tosyloxybenzene can be extracted and added to a solution of aqueous sodium hydroxide (NaOH) and tert-butanol, removing the tosylate protecting group and yielding 4-methoxy-3-iodophenol. The 4-methoxy-3-iodophenol can be extracted and exposed to resin-bound triphenylphosphine ($PPh_3$) in a solution of azopyridine and ethanol ($CH_3CH_2OH$) in a salt bath at 0° C., yielding 4-ethoxy-2-iodomethoxybenzene. The 4-ethoxy-2-iodomethoxybenzene can be extracted and added to a solution of titanium tetrachloride ($TiCl_4$) and 1,1-dichlorodimethylether (CHCl$_2$OCH$_3$) dissolved in dichloromethane (CH$_2$Cl$_2$) in a salt bath at −10° C., yielding 2-ethoxy-4-iodo-5-methoxybenzaldehyde. The 2-ethoxy-4-iodo-5-methoxybenzaldehyde can be added to lithium aluminum hydride (LiAlH$_4$) and methanesulfonyl chloride (CH$_3$SO$_2$Cl) dissolved in pyridine, and then sodium iodide (NaI) and triethyl phosphite (P(OCH$_2$CH$_3$)$_3$) can be added to the reaction mixture, yielding diethyl 2-ethoxy-4-iodo-5-methoxybenzylphosphonate.

Example 3

Synthesis of (E)-(4-(2-ethoxy-4-iodo-5-methoxystyryl)-(2-ethoxy-5-ethylphenyl)ethynyl)tri-iso-propylsilane The 2-methoxy-5-ethoxy-4-((tri-iso-propylsilyl)ethynyl)benzaldehyde and diethyl 2-ethoxy-4-iodo-5-methoxybenzylphosphonate can be added to a solution containing sodium hydride (NaH) dissolved in tetrahydrofuran (THF), yielding (E)-(4-(2-ethoxy-4-iodo-5-methoxystyryl)-(2-ethoxy-5-methylphenyl)ethynyl)tri-iso-propylsilane.

The (E)-((4-(2-ethoxy-4-iodo-5-methoxystyryl)-(2-ethoxy-5-methylphenyl)ethynyetri-iso-propylsilane (E)-(4-(2-ethoxy-4-iodo-5-methoxystyryl)-(2-ethoxy-5-methylphenyl)ethynyl)tri-iso-propylsilane can be extracted and added to a solution of tetra-n-butylammonium fluoride (TBAF) dissolved in tetrahydrofuran (THF) over a palladium catalyst bed, catalyzing a polymerization reaction yielding regioregular poly(aryl ethynyl)-poly(aryl vinyl) (PPVE). A small sample of PPVE can be added to a NMR tube containing a solution of 99.9% deuterated chloroform (CDCl$_3$) and 0.1% tetramethylsilane (TMS). The dissolved PPVE can then be inserted into a proton ($^1$H) NMR spectrometer and undergo analysis to verify the purity and integrity of the resultant compound. The PPVE is expected to exhibit two aromatic peaks and one alkene peak in its NMR spectra.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense of one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense of one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," and the like include the number recited and refer to ranges which can be subsequently broken down into subranges, as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A compound of general Formula III:

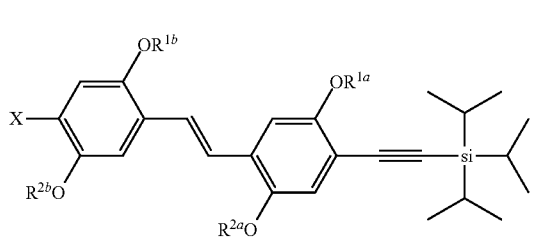

wherein:
each $R^{1a}$, $R^{1b}$, $R^{2a}$, and $R^{2b}$ is, independently, $C_1$-$C_{20}$ alkyl, $C_2$-$C_{20}$ alkene, $C_2$-$C_{20}$ alkyne, or alkylene glycol; and
X is hydroxide, alkoxide, astatine, iodine, bromine, chlorine, or fluorine, triflate($CF_3SO_3$), mesylate ($CH_3SO_3$), tosylate ($CH_3C_6H_4SO_2$), or besylate ($C_6H_5SO_3^-$).

2. The compound according to claim 1, wherein each of $R^{1a}$ and $R^{2a}$ is independently $C_1$-$C_{20}$ alkyl.

3. The compound according to claim 1, wherein each of $R^{1a}$ and $R^{2a}$ is independently $C_1$-$C_6$ alkyl.

4. The compound according to claim 1, wherein each of $R^{1b}$ and $R^{2b}$ is independently $C_1$-$C_{20}$ alkyl.

5. The compound according to claim 1, wherein each of $R^{1b}$ and $R^{2b}$ is independently $C_1$-$C_6$ alkyl.

6. The compound according to claim 1, wherein X is iodine, bromine, chlorine, or fluorine.

7. The compound according to claim 1, wherein $R^{1a}$ is ethyl.

8. The compound according to claim 1, wherein $R^{2a}$ is methyl.

9. The compound according to claim 1, wherein $R^{1b}$ is ethyl.

10. The compound according to claim 1, wherein $R^{2b}$ is methyl.

11. The compound according to claim 1, wherein X is iodine.

12. The compound according to claim 1, wherein the compound is (E)-(4-(2-ethoxy-4-iodo-5-methoxystyryl)-(2-ethoxy-5-methoxyphenyl)ethynyl)tri-iso-propylsilane:

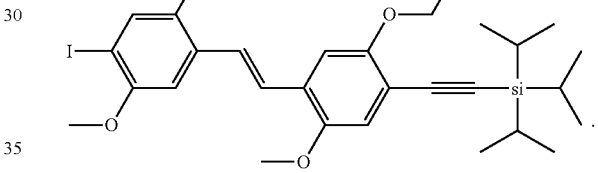

* * * * *